United States Patent
Peng et al.

(10) Patent No.: US 8,160,341 B2
(45) Date of Patent: *Apr. 17, 2012

(54) SYSTEMS AND METHODS FOR AUTOMATIC ROBUST ANATOMY DETECTION THROUGH LOCAL VOTING AND PREDICTION

(75) Inventors: Zhigang Peng, Blue Bell, PA (US); Yiqiang Zhan, Berwyn, PA (US); Xiang Zhou, Exton, PA (US); Arun Krishnan, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 663 days.

This patent is subject to a terminal disclaimer.

(21) Appl. No.: 12/334,898

(22) Filed: Dec. 15, 2008

(65) Prior Publication Data
US 2009/0161937 A1 Jun. 25, 2009

Related U.S. Application Data

(60) Provisional application No. 61/016,313, filed on Dec. 21, 2007, now abandoned.

(51) Int. Cl.
*G06K 9/00* (2006.01)
(52) U.S. Cl. .................. 382/131; 382/128; 382/132
(58) Field of Classification Search .................. None
See application file for complete search history.

(56) References Cited

U.S. PATENT DOCUMENTS

| | | | |
|---|---|---|---|
| 6,674,883 B1 | 1/2004 | Wei et al. | |
| 7,072,435 B2 * | 7/2006 | Metz et al. | 378/8 |
| 2010/0284590 A1 * | 11/2010 | Peng et al. | 382/128 |

OTHER PUBLICATIONS

Mougiakakou et al., "Differential diagnosis of CT focal liver lesions using texture features, feature selection and ensemble driven classifiers", Artificial Intelligence in Medicine, Elsevier, NL, vol. 41, No. 1, Aug. 29, 2007, pp. 25-37.
Kalker et al., "Cardiac Image Segmentation for Contrast Agent Videodensitometry", IEEE Transactions on Biomedical Engineering, IEEE Service Center, Piscataway, NJ, vol. 52, No. 2, Feb. 1, 2005, pp. 277-286.
International Search Report including Notification of Transmittal of the International Search Report, International Search Report, and Written Opinion of the International Searching Authority, Apr. 6, 2009.

* cited by examiner

*Primary Examiner* — Vinh Nguyen
(74) *Attorney, Agent, or Firm* — Peter Withstandley

(57) ABSTRACT

A method for performing a medical imaging study includes acquiring a preliminary scan. A set of local feature candidates is automatically detected from the preliminary scan. The accuracy of each local feature candidate is assessed using multiple combinations of the other local feature candidates and removing a local feature candidate that is assessed to have the lowest accuracy. The assessing and removing steps are repeated until only a predetermined number of local feature candidates remain. A region of interest (ROI) is located from within the preliminary scan based on the remaining predetermined number of local feature candidates. A medical imaging study is performed based on the location of the ROI within the preliminary scan.

20 Claims, 4 Drawing Sheets

SYSTEMS AND METHODS FOR AUTOMATIC ROBUST ANATOMY DETECTION THROUGH LOCAL VOTING AND PREDICTION

CROSS-REFERENCE TO RELATED APPLICATION

The present application is based on provisional application Ser. No. 61/016,313, filed Dec. 21, 2007, the entire contents of which are herein incorporated by reference.

BACKGROUND OF THE INVENTION

1. Technical Field

The present disclosure relates to anatomy detection and, more specifically, to robust anatomy detection though local voting and prediction.

2. Discussion of Related Art

Computed tomography (CT) imaging is the practice of visualizing the internal structure of a subject using a series of x-rays taken at multiple angles, the data from which may be combined and rendered by a computer system for illustrating the internal structure of the subject in three-dimensions. While CT imaging is relatively safe, it does involve exposure to ionizing radiation, which could become harmful in patients. Accordingly, it is generally considered prudent to limit the acquisition of image data to a particular field of the subject's body. By scanning only this field, the patient's exposure to ionizing radiation can be limited and the time needed to acquire the image reduced. Moreover, by limiting the scanning field, it is possible to acquire the desired image data more quickly and with less use of resources than if the entire body was scanned.

It is therefore important to be able to correctly identify the scanning field so that the resulting CT image captures the desired structural data. If the scanning field is selected to be sufficiently large, then there is less risk of missing pertinent structural data. However, the more precise the field is, the faster the scan can be performed and the less the subject is exposed to potentially harmful ionizing radiation. Accordingly, it is desirable to select a precise scanning field that is only as large as is necessary to capture the desired structural data.

In order to set the scanning field, often the CT scanner is used to produce one or more topograms of the subject's body. A topogram is a scout image that may be used to establish where the target organs are located within the subject's body so that the scanning field may be precisely selected. The topogram appears similar to a conventional radiograph, where the outline of the subject's body may be seen with certain organs and anatomical features superimposed thereon.

Presently, the scanning field is manually determined by a human operator such as a radiology technician. The human operator uses learned knowledge of human anatomy to identify the organs to be imaged and then selects the scanning field to be scanned in detail. However, this manual determination may take an amount of time that is noticeable to the subject, and as such, there is a greater possibility that the subject may shift position between the acquisition of the topogram and the acquisition of the CT scan within the manually determined scanning field. Accordingly, the manually determined scanning field must be selected with wide margins to allow for subtle movement. Moreover, the manually selected scanning field may be slightly different each time a CT scan is performed and thus multiple CT scans, such as follow-up studies of the same patient and/or cross-patient comparisons, may be more difficult to compare owing to the inherent inconsistency of the manual field selection.

SUMMARY

A method for performing a medical imaging study includes acquiring a preliminary scan. A set of local feature candidates is automatically detected from the preliminary scan. The accuracy of each local feature candidate is assessed using multiple combinations of the other local feature candidates and removing a local feature candidate that is assessed to have the lowest accuracy. The assessing and removing steps are repeated until only a predetermined number of local feature candidates remain. A region of interest (ROI) is located from within the preliminary scan based on the remaining predetermined number of local feature candidates. A medical imaging study is performed based on the location of the ROT within the preliminary scan.

The preliminary scan may be a scout image that includes a two-dimensional representation of a subject being scanned. The preliminary scan may be a topogram image. The medical imaging study may be a CT scan and the preliminary scan may be a CT topogram image.

The local feature candidates may represent potential anatomical landmarks. The local feature candidates may be automatically detected from the preliminary scan by identifying regions of the preliminary scan that appear to be known anatomical landmarks. The set of local feature candidates may include multiple local feature candidates that appear to be the same anatomical landmark.

The accuracy of each local feature candidate may be assessed by using each combination of other local feature candidates as a voting group, wherein each voting group votes for the each local feature candidate by judging the degree to which the each local feature candidate represents a corresponding local feature wile assuming that the voting group accurately represents corresponding local features. Each voting group may include 1, 2, 3, or more other local feature candidates.

Locating a region of interest (ROI) from within the preliminary scan based on the remaining predetermined number of local feature candidates may include using the remaining predetermined number of local feature candidates as a frame of reference to structurally register the preliminary scan and then finding the region of interest (ROI) within the preliminary scan based on the structural registration.

Each of the multiple combinations of the other local feature candidates may make up a voting group that votes for each local feature candidate in assessing their accuracy and for each iteration of repeating the assessing and removing step. A local feature candidate may be assessed to have the lowest accuracy when it has a lowest vote from among maximum votes received by each of the multiple combinations of the other local feature candidates.

For each iteration of repeating the assessing and removing step, a local feature candidate may be assessed to have the lowest accuracy when it is has a sudden reduction in vote value, as determined by examining the mean of good votes from a most recent iteration.

A method for determining a scanning field for performing a medical imaging study includes receiving a topogram image. A set of local feature candidates is automatically detected from the topogram image. Which of the local feature candidates represent a worst candidate is determined by having a plurality of groups of the local feature candidates vote on each individual local feature candidate, and removing the worst candidate from the set of local feature candidates. The voting and removal are repeated such that one feature candidate is removed from the set at each iteration, until there are only a predetermined number of remaining feature candidates. The scanning field is selected based on the remaining feature candidates.

The local feature candidates may represent potential anatomical landmarks. Voting may be performed by using each combination of other local feature candidates as a voting group. Each voting group may vote for the each local feature candidate by judging the degree to which the each local feature candidate represents a corresponding local feature wile assuming that the voting group accurately represents corresponding local features.

Selecting the scanning field based on the remaining feature candidates may include finding a region of interest (ROI) within the topogram image based on the remaining feature candidates and selecting the scanning field to include the region of interest (ROI).

The region of interest may be found within the topogram image by using the remaining feature candidates as frame of reference to structurally register the topogram image and then finding the region of interest (ROI) within the topogram image based on the structural registration. The region of interest (ROI) to be found may be manually selected by a user.

A computer system includes a processor and a program storage device readable by the computer system, embodying a program of instructions executable by the processor to perform method steps for performing a medical imaging study. The method includes acquiring a topogram image; automatically detecting a set of local feature candidates representing potential anatomical landmarks from the topogram image; assessing the accuracy of each local feature candidate using multiple combinations of the other local feature candidates and removing a local feature candidate that is assessed to have the lowest accuracy; repeating the assessing and removing step until only a predetermined number of local feature candidates remain; locating a provided region of interest (ROI) from within the topogram image based on the remaining predetermined number of local feature candidates; and performing a medical imaging study based on the location of the ROI within the topogram image.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
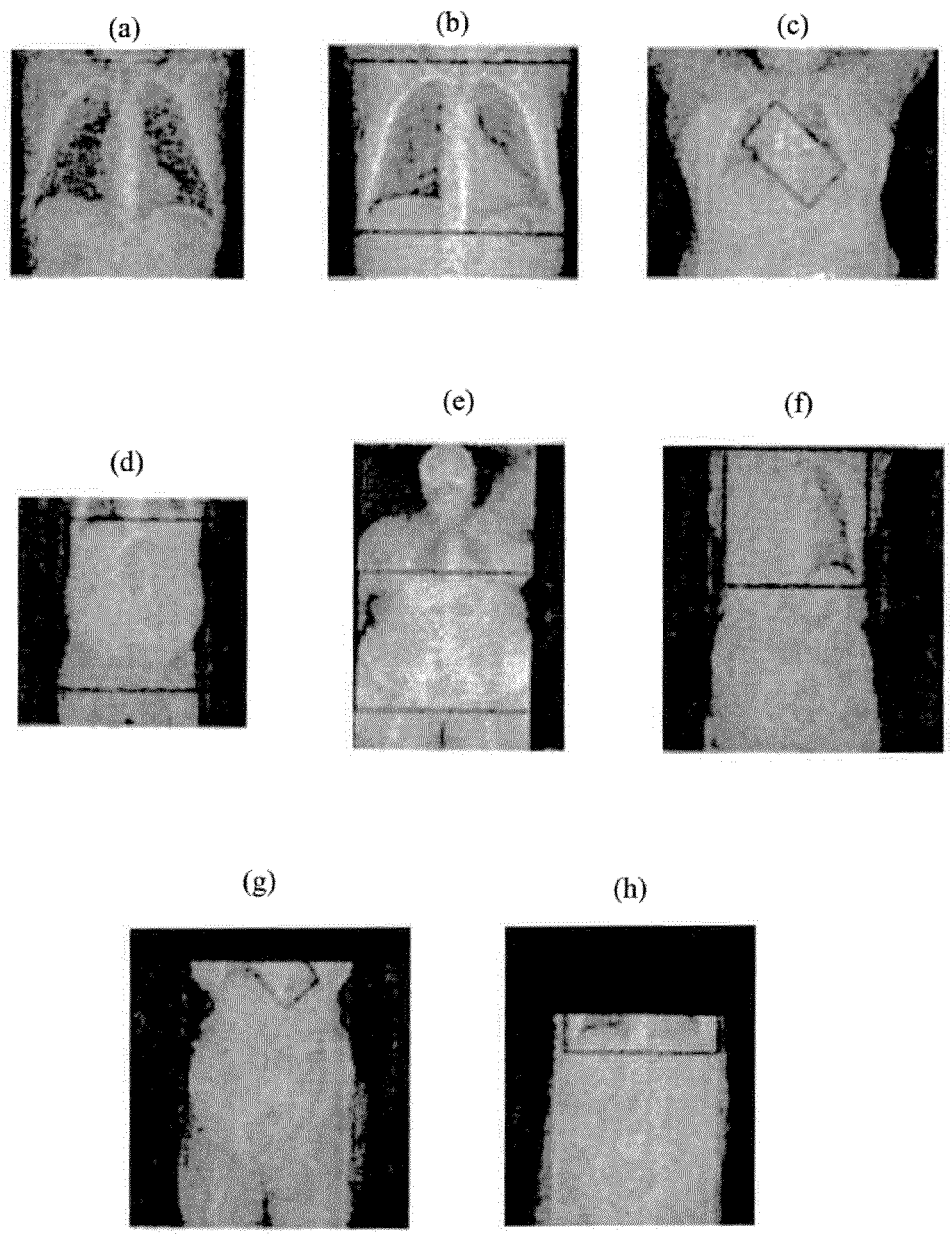
FIGS. 1(a)-(h) are example CT topograms that may be used to automatically determine an appropriate scanning field according to exemplary embodiments of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide an approach for automatically selecting a scanning field within a topogram image for the localization of a CT image study. By automatically selecting the scanning field, rather than having the field manually selected by a human operator, the process of acquiring a CT image may be sped up, made more reliable, and/or provide for a greater level of consistency and/or repeatability.

FIGS. 1(a)-(h) are example CT topograms that may be used to automatically determine an appropriate scanning field according to exemplary embodiments of the present invention. In these topograms, the outline of the subject may be seen with various anatomical structures superimposed thereon. Where present, the determined scanning fields are displayed with black boxes.

The topograms may be relatively low resolution, for example, each image may be 512 pixels by 512 pixels. Because the topogram can be of a relatively low resolution and does not require the sophisticated three-dimensional rendering of a CT scan, the topogram may be acquired relatively quickly and with minimal exposure to ionizing radiation.

Automatically identifying the scanning field may involve registering the topogram against a known anatomical map. Thus proper identification of the scanning field may depend on finding a strong relationship between the anatomical configuration of the subject and that of the anatomical map. One key problem in identifying the scanning field from within a topogram is the fact that the relative size and position of human anatomy can vary widely from subject to subject and from time to time. These variations may cause many heuristic approaches to fail to be able to correctly locate the desired structural features from within the topogram. For example, an obese patient with hands up, as illustrated in FIG. 1(e) may be difficult to automatically detect a scanning field for where the method of registering the structure of the subject depends on skin or head/neck detection.

In addition to variations in the subject's size and proportions, disease may enlarge, shrink, or change the relative position of one or more anatomical structures for which registration depends. Moreover, in addition to normal variations between subjects, many subjects may have an unusual anatomical structure owing to prior surgical treatment and/or congenital defect. For example, FIG. 1(f) is a topogram of a subject with a collapsed or resected lung. It would be difficult to automatically determine a scanning area on such a patient when registration utilizes active shape/appearance modeling such as performing registration based on a determined location of the lung. Additionally, in many partial-body topograms, as much as 80% to 90% of certain anatomical features can be out of the field of view of the topogram. An example of this may be seen in the topogram image of FIGS. 1(g) and (h).

Accordingly, it may be difficult to automatically identify a scanning field with a level of accuracy that is at least as good as when manually identified.

One possible solution to this problem would be to utilize a local feature based approach to register the topogram, for example, as discussed in D. Cristinacce and T. Cootes, *Facial Feature Detection Using Adaboost with Shape Constraints*, In 14th. British Machine Vision Conference, pages 231-240, 2003, which is herein incorporated by reference. In such a solution, shape models are formed to recognize various geometric structures that may be found within the topogram.

There may be multiple shape models for each structure so that a particular anatomical structure may be identified even if its appearance is dissimilar to the most common configuration, so long as these is an existing shape model available that is sufficiently similar. According to this approach, multiple hypotheses of each local feature may be screened using the predetermined shape models and a winning hypothesis may be determined for each feature. Missing features may then be predicted using the model.

If a feature detector produces only false hypotheses, the shape model may reject all configurations and thus insufficient structural identification may be provided. Unfortunately, where patients have significant structural abnormalities such as tumors and/or full organ resection, local feature based registration may fail to provide adequate structural identification.

In an attempt to solve the problem of detecting anatomical structure in the even of partial obstruction or the case where a portion of a structure is beyond the field of view, sparse, part-based representation may be used to identify local features, for example, as discussed in S. Agarwal, A. Awan, and D. Roth, *Learning to Detect Objects in Images via a Sparce, Part-based reresentation, IEEE Trans. PAMI*, 26(11):1475-1490, 2004, which is herein incorporated by reference. Here, a global constraint may be imposed through the learning process of creating shape models. Thus, structural identification may be possible in the presence of mild occlusion. However, severe occlusion, for example, in the range of 80% to 90%, may still prevent proper detection of anatomical structure. Moreover, the accuracy of this approach, which may be based on a single consolidated global decision, may not satisfy the local accuracy requirement of the topogram application.

In performing structural identification using local features, graph matching may be used to evaluate competing constellations of local features, for example, as discussed in T. Leung, M. Burl, and P. Perona, *Finding Faces in Cluttered Scenes Using Random Labeled Graph Matching, Proc. Fifth IEEE Int'l Conf. Computer Vision*, pages 637-644, 1995, which is herein incorporated by reference. Here, a graph may be constructed to model the mutual dependency in terms of mean and variance of distance. Pruning strategies may be applied to limit the number of candidate constellations. For example, the local detector confidence may be used to elect a set of "strong features" as leads.

However, such techniques may result in false detections that have a high level of confidence.

Other techniques may perform pedestrian detection using separate support vector machine (SVM) classifiers to detect body parts such as heads, arms and legs, for example, as discussed in A. Mohan, C. Papageorgiou, and T. Poggio, *Example-Based Object Detection in Images by Components, IEEE Trans. PAMI*, 23(4):349-361, 2001, which is herein incorporated by reference. Here, a second SVM classifier may integrate the detected parts to make a decision as to whether a person has been detected. Such techniques may be useful even in the event of partial occlusion or where there is little contrast between people and backgrounds. However, such techniques may not be useful in identifying a subset of valid local features to draw the regions of interest, as may be required to automatically identify a scanning field, as in such techniques, the black-box nature of the SVM classifier gives no information as to which local features might be invalid.

As discussed above, before the CT examination is performed, a topogram is acquired to aid in the determination of a scanning field. The scanning field generally coincides with a region of interest (ROI) that includes, for example, an organ that is to be examined. An ROI may be defined by a few well-known anatomical landmarks. For example, the abdomen ROI may range from the upper dome of the diaphragm to the symphysis pubis. In FIG. 1, the ROIs, and thus the scanning fields, may be represented as a black box, for example, as seen in FIGS. 1(*b*), (*c*), (*d*), (*e*), (*f*), (*g*), and (*h*). The ROIs may have boundaries that are parallel and perpendicular to the sides of the topogram, as seen in FIGS. 1(*b*), (*d*), (*e*), (*f*), and (*h*) or the ROIs may be slanted as seen in FIGs. (*c*) and (*g*). Moreover, the ROIs may be fully contained within the topogram, as seen in FIGS. 1(*b*), (*c*), and (*d*) or the ROIs may be partially out of view as seen in FIGS. 1(*g*) and (*h*).

Examples of common ROIs may include the lungs, heart, abdomen, liver, pelvis, etc.

Exemplary embodiments of the present invention seek to automatically detect the set of ROIs, $\mathfrak{R}=\{r_k\}$ from the topogram, even where one or more of the ROIs are only partially present. Then the scanning field for the CT study may be automatically defined based on the detected ROIs. In detecting the ROIs, a local feature-based approach may be used. This may be accomplished by identifying a set of landmarks and judging the accuracy of each landmark by relation to a group of other landmarks. This judgment is referred to herein as a "vote" and each landmark is voted upon by one or more combinations of other landmarks that are referred to herein as "voting groups."

Thus, the local features may be used as the set of anatomical landmarks, X, where $|X|=N$. A local voting algorithm may then be used to produce an indicator array $\Omega=\{\omega_i\}$, where $|\Omega|=N$ and $\omega_i \in \{0,1\}$, and where:

$$\omega_i = \begin{cases} 1 & \text{if landmark } x_i \text{ is elected,} \\ 0 & \text{if landmark } x_i \text{ is voted out.} \end{cases} \quad (1)$$

The local voting process may be formulated as follows:

$$\Omega^* = \operatorname{argmax} \sum_{i=1}^{N} \omega_i \times \Gamma(x_i \mid X \setminus x_i) \quad (2)$$

where $\Gamma(x_i|X\setminus x_i)$ represents the best "vote" received by $x_i$, $\|\Omega\|_1 = \sum_{i=1}^{N} \omega_i$, and M<N is the desired number of remaining landmarks. Voting is described in greater detail below.

As used herein, $\tilde{X}$ denotes the set of elected landmarks $\tilde{X}=\{x_i|\omega_i=1\}$. The result of the voting is to predict the ROIs using a subset of the elected landmarks $\tilde{X}$. Each ROI $r_k$ may be predicted according to the formula:

$$r_k = \wp_k(\tilde{X}) \quad (3)$$

where $\wp_k()$ first selects a best subset from $\tilde{X}$, and then predicts ROI $r_k$. This ROI prediction mechanism is described in greater detail below.

Figure 2:
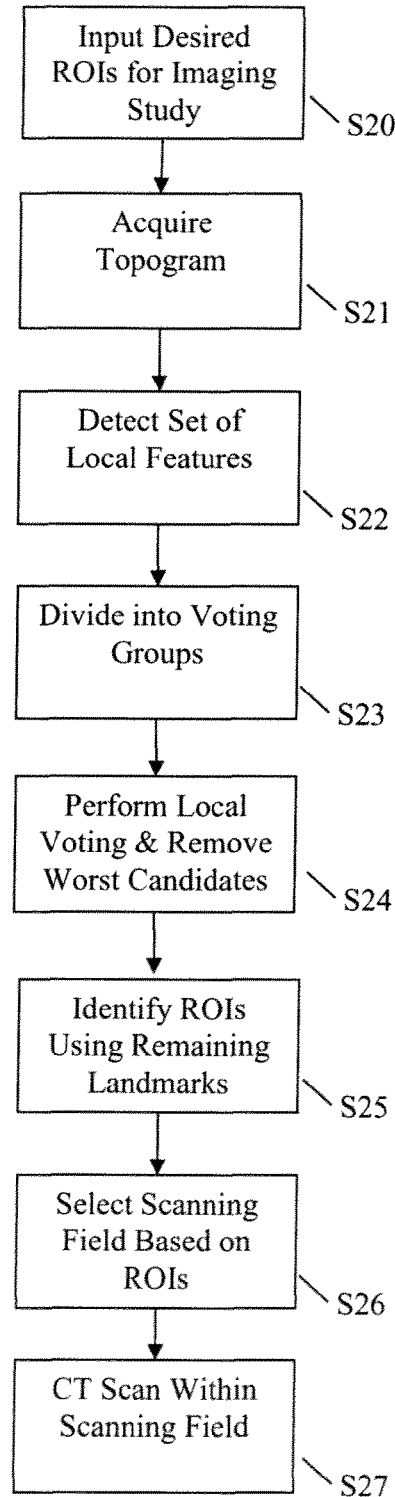
FIG. 2 is a flow chart illustrating a method for automatically detecting a scanning field according to an exemplary embodiment of the present invention.

FIG. 2 is a flow chart illustrating a method for automatically detecting a scanning field according to an exemplary embodiment of the present invention. First, the topogram is acquired (Step S21). As discussed above, the topogram is a scout image that includes a two-dimensional representation of the subject. The topogram may be acquired using a particular modality of the same imaging device that is used to acquire the detailed medical image data. Next, a set of local features are detected (Step S22). Each local feature may be an anatomical landmark that is observable from the topogram. The set of local features may be a redundant set of local features, X, that are detected with multiple hypotheses. This is to say that there may be multiple local features detected for the same anatomical landmark whereby each of the local features is obtained based on a different set of assumptions for identifying the feature.

Next, the set of local features X, or landmarks, may be divided into subsets of spatially consistent local features $\hat{X}$, or voting groups, where $\hat{X} \subset X$ (Step S23). The goal may be to select a subset of most reliable features $\hat{X}$ and predict the ROIs and thus the scanning field, based on the set of most reliable features $\hat{X}$. Exemplary embodiments of the present invention find the subset of most reliable features $\hat{X}$ by removing each of the worst match landmark features until all that is left is the subset of most reliable features. Thus, rather than attempting to find a single best constellation of landmarks that may be indicative of the ROI, exemplary embodiments of the present invention pare away the worst matches. This may be especially beneficial, as it is possible for a poor landmark constellation to be incorrectly identified as a best match, as is described in detail below.

This assessment as to the quality of each landmark candidate is referred to herein as "local voting." Accordingly, after the landmarks have been divided into the voting groups $\hat{X}$ (Step S23), local voting is performed to assess the relative quality of each candidate (Step S24).

As discussed above, each landmark is considered a candidate for the most reliable feature set. The quality of a candidate is voted upon by voting groups formed by other landmarks.

Each landmark may participate as an individual voter and may also form voting groups with other landmarks. Each "vote" may be a binary variable, for example, a high vote may equal "1" and a low vote may equal "0" or each vote may be a real number, for example, a conditional probability. The higher the vote, the more likely the candidate is to be a good feature.

Assuming the size of each voting group is L, each landmark may receive $C_{N-1}^L$ number of votes. A voting group may be small, for example, with L=1, 2, or 3. For example, a voting group may include only two other landmarks. Alternatively, each voting group may include a large number of landmarks, with $L \geq 4$. Exemplary embodiments of the present invention may be explained in terms of voting groups of 2 landmarks for the purposes of simplifying the explanation so that greater attention may be paid to the reasoning strategy behind the voting. However, it is to be understood that the voting groups may be made up of any number of other landmarks, and it may also be possible to utilize voting groups of dissimilar size.

In voting (Step S24), each voting group may designate each candidate with a high vote or a low vote. However, each voting group may its self be either a "good" voting group or a "bad" voting group. A voting group is "good" if all of its members are good voters, and a voting group is "bad" if all of its members are bad voters. A voter is good if it can correctly give a good candidate a high vote and a bad candidate a low vote thereby productively helping to determine the ROI. Meanwhile, a voter is bad if it either fails to give a good candidate a high vote or fails to give a bad candidate a low vote thereby being counterproductive in determining the ROI. There are many reasons why a voter would be counterproductive, and some of these reasons are discussed in detail below. It may also be possible that for a given voting group, some voters are good and others are bad. Such a voting group may be considered a "mixed group."

As discussed above, where the ROI is attempted to be found using a single best constellation of landmarks, the possibility exists that bad landmarks are selected for use because of various voting behavior models that tend to allow for bad landmarks to be judged positively. Exemplary embodiments of the present invention can avoid this trapping by removing bad candidates form consideration prior to selecting the landmarks to use.

As discussed above, there are various voting behavior models that would tend to rate bad candidates positively when not using exemplary embodiments of the present invention. For example, according to the naive model, the "naive" voter group would assign a low vote to all candidates, regardless of whether they are good or bad. According to the Mafia model, however, there can be a collection of candidates/voters that are in truth bad, but tend to give high votes to other members of the same collection. In this way, bad voters may make each other look good. This may happen, for example, when a set of erroneous landmarks form a legitimate constellation. However, a good voter may be used to veto any bad candidate. According to the Mafia plus corrupted citizen model, however, it is possible that a voter that is not within the collection of candidates bad that self-validate, can also provide a high vote to the collection of bad candidates.

In light of these various voting behavior models, exemplary embodiments of the present invention "peel away" bad candidates so that they cannot be used to vote on remaining candidates. While this may be achieved using any number of strategies, two exemplary strategies are discussed in detail below. It is to be understood that similar strategies may be used based on the two strategies explained below. For example, elements of each strategy may be combined to provide additional strategies.

According to a first strategy, a "weakest link" is iteratively removed from the pool of voters. Each candidate receives votes from various combinations of the other candidate-voters. A maximum vote is the highest vote score attributed to the candidate under review from among the voters. Thus, this value is the best vote that the candidate received. In each iteration, the maximum votes received by all remaining candidates are compared. The candidate whose maximum vote is minimum across all the remaining candidates is removed. The candidate whose best vote is minimum may be considered a "weakest link" and may therefore be removed. This process may be repeated until the number of the remaining candidates reaches a predetermined value M. Thus it is assumed that there are at least M good candidates and that all of the bad candidates can be removed as weakest links. This weakest link removal strategy may work well when faced with candidates of the naive behavior model.

Exemplary pseudo code for implementing the weakest link is provided below in Table 1:

TABLE 1 for each candidate $x_i$ do
   for each combination of $X \backslash x_i$ do
     Compute the vote of $x_i$
   end for
   sort all the votes received by landmark $x_i$ (The sorted array is defined by $\gamma_{x_i}$).
end for
repeat
   $\tilde{x} = \arg\min_{x_i} \max \gamma_{x_i}$
   Remove $\tilde{x}$ and all votes involved with $\tilde{x}$.
until Only M candidates are left According to a second strategy, a transverse pointer h is used to progress forward and backward checking the $h^{th}$ maximum vote for each candidate as h progresses. In the forward stage, h moves along the sequence $\{C_{j-1}^L+1 | j = L+1, \ldots, N+1\}$, where the size of the voting group and candidates set are L and N, respectively. The $h^{th}$ maximum vote for each candidate may be checked. A substantial vote drop found before h=L+1 may indicate that the corresponding candidate is a member of a mafia collection. A vote drop is a sudden reduction in a vote value. A vote drop may be determined, for example, as described in detail below.

Accordingly, the candidate that has experienced a vote drop may be removed from consideration. After removal, h may start to go backward to prune other members of the mafia collection. This process may be repeated until there are no more vote drops found and thus no more mafia collections. When L=2, the sequence that h traverses, first forward and then backward, may be called the Lazy Caterer's Sequence or the central polygonal numbers, hence, this strategy may be called the Lazy Caterer's strategy.

Exemplary pseudo code for implementing the Lazy Caterer's strategy is provided below in Table 2:

TABLE 2

```
for each candidate x_i do
    for each combination of X\x_i do
        Compute the vote of x_i
    end for
    sort all the votes received by landmark x_i
    (The sorted array is defined by γ_{x_i}).
end for
```

$$T(\gamma_{x_i}) = \frac{\sum_{x_i} \max(\gamma_{x_i})}{N}$$

```
j_max = L + 1
for j from j_max to N/2 - 1 do
    h = C_{j-1}^L + 1
    x̌ = argmin_{x_i} γ_{x_i}[h]
```

$$\text{if } \gamma_{\check{x}}[h] < \frac{T(\gamma_{x_i})}{3} \text{ then}$$

```
        if j_max < j then
            j_max = j
        end if
        Remove all votes involved with x̌.
        j = j - 1.
        N = N - 1.
        Continue
    end if
```

$$T(\gamma_{x_i}) = \frac{\sum_{x_i} \gamma_{x_i}[h]}{N}$$

```
end for
```

For the pseudo code of Table 2, the $$\frac{T(\gamma_{x_i})}{3}$$

term is an adaptive threshold for detecting the substantial vote drop, where $T(\gamma_{x_i})$ is the mean of the good votes in the last iteration. The selected denominator "3" of this term may be changed to suit the needs of the particular vote function and/or problem being solved.

The Lazy Caterer's strategy may thus be used to overcome the problem associated with the naive model, the mafia model, and/or the mafia plus corrupted citizen model. Accordingly, the above-described weakest link strategy and/or the Lazy Caterer's strategy may be used to perform local voting to assess the relative quality of each candidate (Step S24). In this step, as described above, weakest voters are removed until there are only a predetermined number of voters remaining. These remaining voters may then be used to automatically identify the desired ROIs from within the topogram image (Step S25). As the ROIs represent regions of interest within the body of the subject that are to be the focus of the imaging study, the medical practitioner may input the desired organs and/or other anatomical structures that are to be treated as ROIs (Step S20). For example, if the medical practitioner desires that the lungs be imaged, the medical practitioner can establish the lungs as ROIs. This selection of ROIs may occur prior to the acquisition of the topogram image (Step S21) where it is desired that the length of time between the acquisition of the topogram (Step S21) and the acquisition of the medical image study (Step S27) be minimized, however, it may also be possible to select the desired ROIs after the topogram is acquired.

After the ROIs have been automatically identified within the topogram (Step S25), the goal is to perform the medical image study in such a way as to include the identified regions of interest. However, the scanning field often has a more normal shape than the shape of the one or more ROIs that are to be imaged. For example, the scanning field may be a rectangle. Accordingly, after the ROIs have been identified, a scanning field may be automatically selected that includes the identified ROIs (Step S26). Then, the medical image study may be performed within the selected scanning field (Step S27). The medical image study may be, for example, a CT scan.

Figure 3:
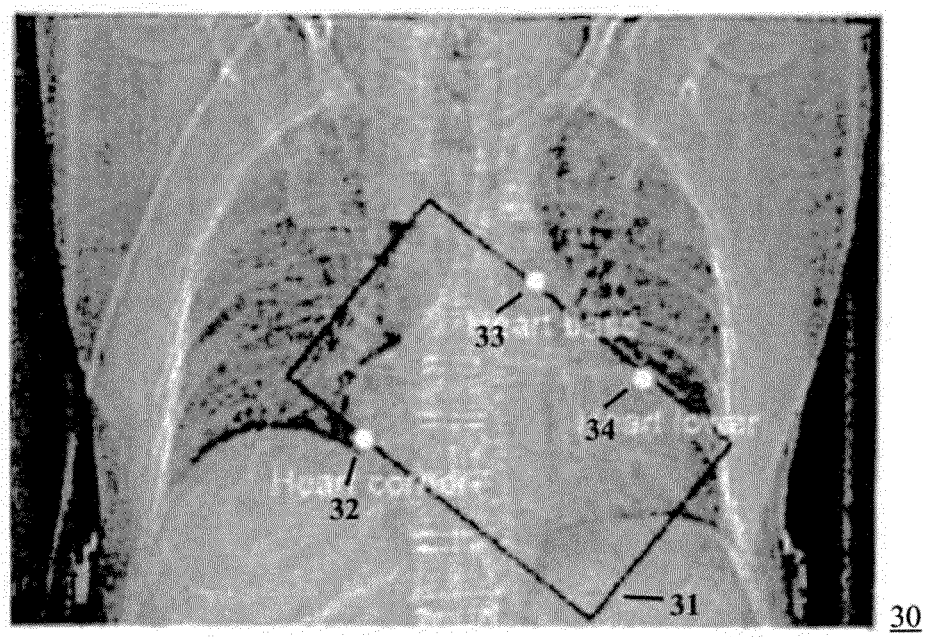
FIG. 3 is an example topogram image where a scanning filed box is drawn to include the heart as an ROI.

The scanning field may be automatically selected based on the ROIs either in accordance with a predetermined protocol or by drawing a box to cover the ROIs with the smallest possible size. In drawing the box, any angle may be used to achieve the smallest possible sized box that includes the full ROIs. Where the scanning field box is drawn in accordance with a predetermined protocol, the protocol may provide for drawing the box that crosses predetermined landmarks. For example, when the ROI in question is the heart, a scanning field box 31 may be drawn to cross the heart corner landmark 32, the heart base landmark 33, and the i heart lower landmark 34, as can be seen in FIG. 3, which is an example of a topogram image 30 where the scanning field box 31 is drawn to include the heart as an ROI.

Similarly, where the lung and heart are the ROIs to be imaged, the scanning field box may be drawn to cover the following seven landmarks: left lung corner, right ling corner, left lung apex, right lung apex, heart corner, heart base, and heart lower. Where the ROIs include the abdomen, liver, and pelvis, the scanning field box may be drawn to cover the following four additional landmarks: the left diaphragm dome, right diaphragm dome, liver base, and symphysis pubis.

Voting according to exemplary embodiments of the present invention will now be described in greater detail. However, it is to be understood that the voting process discussed herein is an example of a voting process that may be used, and that those of ordinary skill in the art may be able to utilize other voting processes.

The vote received by a candidate $x_i$ may be denoted by $\eta(x_i|X_v)$ where $X_v$ is a voting group. The vote may be defined as a likelihood between candidate $x_i$ and its estimation $v_i$ coming from the voting group. The likelihood function may be modeled as a multi-variance Gaussian function, for example, as follows:

$$\eta(x_i \mid X_v) = \frac{1}{(2\pi)^{N/2}|\Sigma|^{1/2}} e^{-(x_i-v_i)^T \Sigma^{-1}(x_i-v_i)} \quad (4)$$

where Σ is the covariance matrix, and the estimation $v_i$=M× $[X_v]$. Here $[X_v]$ is the array of the x, y coordinate of $X_v$ and M is the transform matrix computed from a training set.

In voting, the erroneous landmarks may be considered to be outliers and the remaining good landmarks may be considered to be inliers. Thus, the process of selecting inliers may be considered an outlier removal problem.

As discussed above, prediction of the ROIs $r_k$, may be performed by selecting the best subset $\hat{X}$ from the landmarks X and using only the best subset to compute the ROIs. The ROIs $r_k$, may be represented by a set of parameters $\theta_k$, which may be computed according to the following equation:

$$\theta_k = \xi \times [\hat{X}] \quad (5)$$

where $[\hat{X}]$ is the array of the x, y coordinates in $\hat{X}$.

The transformation matrix $\xi$ may be computed from the training sets by the given ground truth parameters $\theta_k^*$ from the set of landmarks X' by using the minimum error criterion to estimate $\xi$, for example:

$$\xi = (\theta_k^* \times [X']^T)([X'] \times [X'])^{-1} \quad (6)$$

The covariance matrix may also be computed from [X]' and $\theta_k^*$. The covariance matrix, once computed, may then be used to determine whether a landmark subset $\hat{X}$ is good or bad. The landmark subset with the minimum covariance value may then be used to predict the location of the ROIs.

Figure 4:
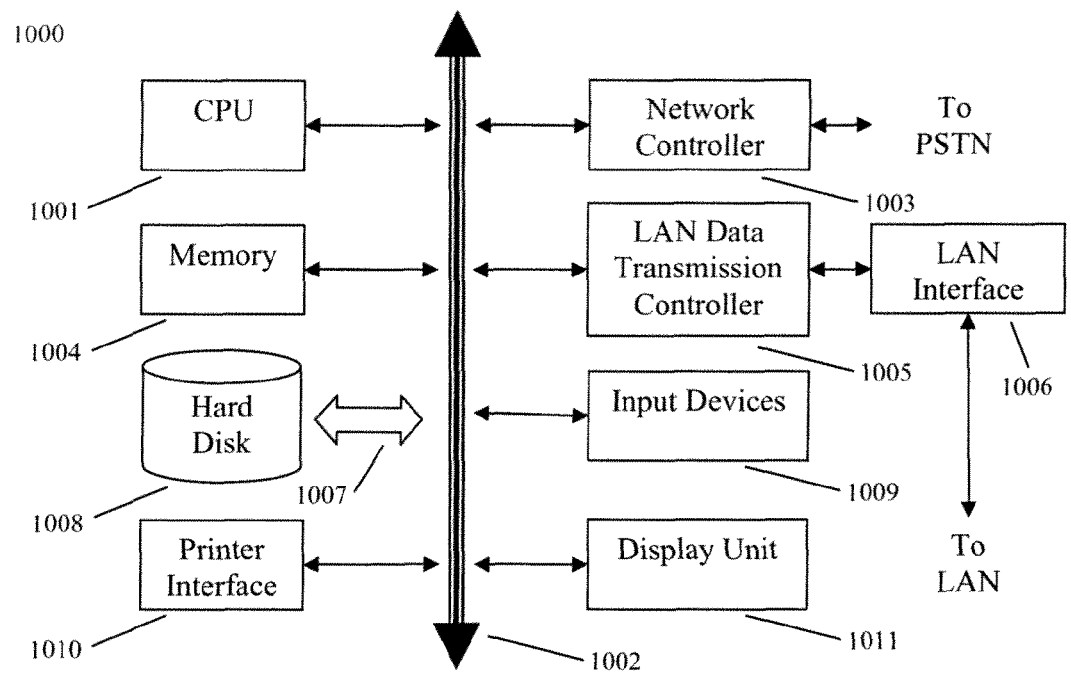
FIG. 4 shows an example of a computer system capable of implementing the method and apparatus according to embodiments of the present disclosure.

FIG. 4 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface oil 1010, a display unit 1011, a local area network (LAN) data transmission controller 1005, a LAN interface 1006, a network controller 1003, an internal bus 1002, and one or more input devices 1009, for example a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for performing a medical imaging study by a computer system comprising:
   acquiring from a scanner, a preliminary scan of a patient;
   automatically detecting, by processor, a set of local feature candidates from the preliminary scan;
   assessing, by the processor, the accuracy of each local feature candidate using multiple combinations of the other local feature candidates and removing a local feature candidate that is assessed to have the lowest accuracy;
   repeating, by the processor, the assessing and removing step until only a predetermined number of local feature candidates remain;
   locating, by the processor, and outputting by a display a region of interest (ROI) from within the preliminary scan based on the remaining predetermined number of local feature candidates; and
   performing a medical imaging study based on the location of the ROI within the preliminary scan.

2. The method of claim 1, wherein the preliminary scan is a scout image that includes a two-dimensional representation of a subject being scanned.

3. The method of claim 2, wherein the preliminary scan is a topogram image.

4. The method of claim 1, wherein the medical imaging study is a CT scan and the preliminary scan is a CT topogram image.

5. The method of claim 1, wherein the local feature candidates represent potential anatomical landmarks.

6. The method of claim 1, wherein the local feature candidates are automatically detected from the preliminary scan by identifying regions of the preliminary scan that appear to be known anatomical landmarks.

7. The method of claim 6, wherein the set of local feature candidates includes multiple local feature candidates that appear to be the same anatomical landmark.

8. The method of claim 1, wherein the accuracy of each local feature candidate is assessed by using each combination of other local feature candidates as a voting group, wherein each voting group votes for the each local feature candidate by judging the degree to which the each local feature candidate represents a corresponding local feature wile assuming that the voting group accurately represents corresponding local features.

9. The method of claim 8, wherein each voting group includes 1, 2 or 3 other local feature candidates.

10. The method of claim 8, wherein each voting group includes 4 or more other local feature candidates.

11. The method of claim 1, wherein locating a region of interest (ROI) from within the preliminary scan based on the remaining predetermined number of local feature candidates includes using the remaining predetermined number of local feature candidates as frame of reference to structurally register the preliminary scan and then finding the region of interest (ROI) within the preliminary scan based on the structural registration.

12. The method of claim 1, wherein each of the multiple combinations of the other local feature candidates comprises a voting group that votes for each local feature candidate in assessing their accuracy and for each iteration of repeating the assessing and removing step, a local feature candidate is assessed to have the lowest accuracy when it has a lowest vote from among maximum votes received by each of the multiple combinations of the other local feature candidates.

13. The method of claim 1, wherein for each iteration of repeating the assessing and removing step, a local feature candidate is assessed to have the lowest accuracy when it is has a sudden reduction in vote value, as determined by examining the mean of good votes from a most recent iteration.

14. A method for determining a scanning field for performing a medical imaging study comprising:
   receiving, from a medical imaging device, a topogram image of a patient;
   automatically detecting, by a processor, a set of local feature candidates from the topogram image;
   determining, by the processor, which of the local feature candidates represent a worst candidate by having a plurality of groups of the local feature candidates vote on each individual local feature candidate, and removing the worst candidate from the set of local feature candidates;

repeating, by the processor, the voting and removal such that one feature candidate is removed from the set at each iteration, until there are only a predetermined number of remaining feature candidates; and selecting, by the processor, and outputting by a display the scanning field based on the remaining feature candidates.

15. The method of claim 14, wherein the local feature candidates represent potential anatomical landmarks.

16. The method of claim 14, wherein voting is performed by using each combination of other local feature candidates as a voting group, wherein each voting group votes for the each local feature candidate by judging the degree to which the each local feature candidate represents a corresponding local feature wile assuming that the voting group accurately represents corresponding local features.

17. The method of claim 14, wherein selecting the scanning field based on the remaining feature candidates includes finding a region of interest (ROI) within the topogram image based on the remaining feature candidates and selecting the scanning field to include the region of interest (ROI).

18. The method of claim 17, wherein the region of interest is found within the topogram image by using the remaining feature candidates as frame of reference to structurally register the topogram image and then finding the region of interest (ROI) within the topogram image based on the structural registration.

19. The method of claim 17, wherein the region of interest (ROI), to be found is manually selected by a user.

20. A computer system comprising:

a processor; and a program storage device readable by the computer system, embodying a program of instructions executable by the processor to perform method steps for performing a medical imaging study, the method comprising:

acquiring a topogram image;

automatically detecting, by the processor, a set of local feature candidates representing potential anatomical landmarks from the topogram image;

assessing, by the processor, the accuracy of each local feature candidate using multiple combinations of the other local feature candidates and removing a local feature candidate that is assessed to have the lowest accuracy;

repeating, by the processor, the assessing and removing step until only a predetermined number of local feature candidates remain;

locating, by the processor and outputting by a display a provided region of interest (ROI) from within the topogram image based on the remaining predetermined number of local feature candidates; and performing a medical imaging study based on the location of the ROI within the topogram image.

* * * * *